United States Patent [19]
Tadmori

[11] Patent Number: 6,022,536
[45] Date of Patent: *Feb. 8, 2000

[54] COMBINED USE OF INTERLEUKIN 10 AND CYCLOSPORIN FOR IMMUNOSUPPRESSION THERAPY

[75] Inventor: Waleed Tadmori, Berkeley Heights, N.J.

[73] Assignee: Schering Corporation, Kenilworth, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/694,973

[22] Filed: Aug. 9, 1996

Related U.S. Application Data
[60] Provisional application No. 60/002,057, Aug. 9, 1995.

[51] Int. Cl.[7] .................................................. A61K 38/19
[52] U.S. Cl. .............................. 424/85.2; 514/2; 514/8; 514/12; 514/21; 514/885
[58] Field of Search ...................... 424/10, 85.2

[56] References Cited

U.S. PATENT DOCUMENTS

| | | | |
|---|---|---|---|
| 4,117,118 | 9/1978 | Härri et al. | 424/177 |
| 4,996,193 | 2/1991 | Hewitt et al. | 514/11 |
| 5,013,719 | 5/1991 | Bowlin | 514/11 |
| 5,328,989 | 7/1994 | Vellekamp et al. | 530/351 |
| 5,430,017 | 7/1995 | Antalné et al. | 514/9 |
| 5,543,393 | 8/1996 | Kim et al. | 514/11 |

FOREIGN PATENT DOCUMENTS

| | | |
|---|---|---|
| WO 93/17698 | 9/1993 | WIPO . |
| WO 94/08606 | 4/1994 | WIPO . |
| WO 94/17773 | 8/1994 | WIPO . |

OTHER PUBLICATIONS

Tadmori et al., 1994, *Cytokine*, 6:462–471.

Primary Examiner—Garnette D. Draper
Attorney, Agent, or Firm—Cynthia L. Foulke

[57] ABSTRACT

A combination of interleukin 10 and cyclosporin is used to suppress graft-versus-host disease, autoimmune diseases and tissue/graft rejection. It has been discovered that administration of a combination of interleukin 10 and cyclosporin causes synergistic suppression of T cell proliferation. Concurrent use of both agents avoids the toxicity associated with higher doses of cyclosporin.

14 Claims, 1 Drawing Sheet

COMBINED USE OF INTERLEUKIN 10 AND CYCLOSPORIN FOR IMMUNOSUPPRESSION THERAPY

This application claims the benefit of U.S. Provisional Application 60/002,057, filed Aug. 9, 1995.

FIELD OF THE INVENTION

The invention relates to a method of suppressing graft/tissue rejection, graft-versus-host disease and autoimmune diseases. In particular, the invention relates to the combined use of interleukin 10 and cyclosporin for immunosuppression therapy.

BACKGROUND OF THE INVENTION

Interleukin 10 (IL-10), a cytokine produced by T lymphocytes, was first identified by its ability to inhibit interferon gamma (IFN-γ) and IL-2 synthesis by mouse and human T lymphocytes. Fiorentino et al., 1989, *J. Exp. Med.* 170:2081–2089; Moore et al., 1990, *Science* 248:1230–1252; Vieira et al., 1991, *Proc. Natl. Acad. Sci. USA* 88:1172–1177. IL-10 was subsequently shown to be produced by B cells (O'Garra et al., 1990, *Internat. Immunol.* 2:821–828) and macrophages (Fiorentino et al., 1991, *J Immunol.* 147:3815–3822).

IL-10 exerts a wide range of effects on a variety of cell types. IL-10 inhibits the synthesis of a wide spectrum of cytokines produced by T cells and monocytes. In addition to inhibiting the synthesis of IFN-γ and IL-2, IL-10 has also been shown to inhibit production of the monokines IL-1α, IL-1β, IL-6 and TNFα de Waal et al., 1991, J. Exp. Med. 174:1209–1217. IL-10 has growth promoting effects on murine thymocytes and T cells (MacNeil et al., 1990, *Immunol.* 145:4167) and mast cells (Thompson-Snipes et al., 1991, *J Exp. Med.* 173:507–512), and it stimulates cytotoxic T-cell development (Chen and Zlotnik, 1991, *J. Immunol.* 147:528–533).

Mouse and human IL-10 have high sequence similarity with a protein encoded by an open reading frame in the Epstein-Barr Virus. The expression product of this open reading frame, named viral IL-10, also has the capacity to inhibit cytokine synthesis. Moore et al., 1990, *Science* 248:1230–1252; Vieira et al., 1991, *Proc. Natl. Acad. Sci. USA* 88:1172–1177.

Several cytokines, including IL-2, IFN-γ and TNFα, have been shown to regulate the mixed lymphocyte reaction (MLR). Shevach, 1985, *Annu. Rev. Immunol.* 3:397; Fidelus et al., 1982, *Transplantation* 34:308; Tadmori et al., 1985, *J. Immunol.* 134:4542–4550; Tadmori et al., 1986, *J. Immunol.* 136:1155–1162; Novelli et al, 1991, 147:1445–1450; Landolfo et al., 1985, *Science* 229:176–2180; Shalaby et al., 1988, *J. Immunol.* 141:499–505. It has been reported that IFN-γ may pay an important role in MLR graft rejection. Novelli et al., 1991, *J. Immunol.* 147:1445–1450; Landolfo et al., 1985, *Science* 229:176–180. Antibodies to IFN-γ or to TNF (Shalaby et al., 1988, *J. Immunol* 141:499–505) have been shown to block MLR-induced proliferation. In these studies it was found that antibodies to IFN-γ suppressed the MLR in human systems as well as allograft reactivity in vitro and in vivo in the mouse.

International Application Publication No. WO 93/17698 discloses the use of IL-10 to suppress tissue graft rejection. The use of both human IL-10 and viral IL-10 is described.

Cyclosporin (also known as cyclosporin A; CSA), a cyclic peptide produced by the fungus *Tolypocladium inflatum* Gams and other fungi imperfecti, has cytokine inhibition ability. It has been found that inhibition of IL-2 production by cyclosporin (Shevach, 1985, *Annu. Rev. Immunol.* 3:397; Fidelus et al., 1982, *Transplantation* 34:308), or an antibody of CD2 (Tadmori et al., 1985, *J. Immunol.* 134:4542–4550) depresses T-cell proliferation induced by a MLR (Tadmori et al., 1986, *J. Immunol.* 136:1155–1162). CSA suppresses in vivo and in vitro cell-mediated responses (Fidelus et al., 1982, Transplantation 34:308–311) and is currently being used in most organ transplantation immunosuppressive protocols. CSA prolongs survival of allogeneic transplants involving skin, heart, kidney, pancreas, bone marrow, small intestine and lung and is also known to suppress graft-versus-host disease (GVHD) and delayed-type hypersensitivity. A problem with CSA, however, is organ toxicity. High doses of CSA can cause profound and irreversible nephrotoxicity as well as hepatoxicity and cardiotoxicity. There thus exists a need for an immunosuppressant treatment method that will allow administration of lower levels of CSA, thereby reducing the toxic effects of this agent.

SUMMARY OF THE INVENTION

The current invention fills this need by providing such a method. More particularly, this invention provides a method for suppressing tissue or organ rejection comprising administering an effective amount of interleukin 10 and cyclosporin to a patient experiencing or at risk of tissue graft rejection.

This invention further provides a method for suppressing graft-versus-host disease comprising administering an effective amount of interleukin 10 and cyclosporin to a patient afflicted with or at risk for graft-versus-host disease.

Still further, this invention provides a method for treating autoimmune diseases comprising administering an effective amount of interleukin 10 and cyclosporin to a patient afflicted with an autoimmune disease.

Pharmaceutical compositions comprising a combination of IL-10 and CSA are also provided by this invention.

BRIEF DESCRIPTION OF THE DRAWING FIGURE

FIG. 1 shows that certain combined doses of human IL-10 and cyclosporin act synergistically to suppress T cell proliferation.

DETAILED DESCRIPTION OF THE INVENTION

Figure 1:
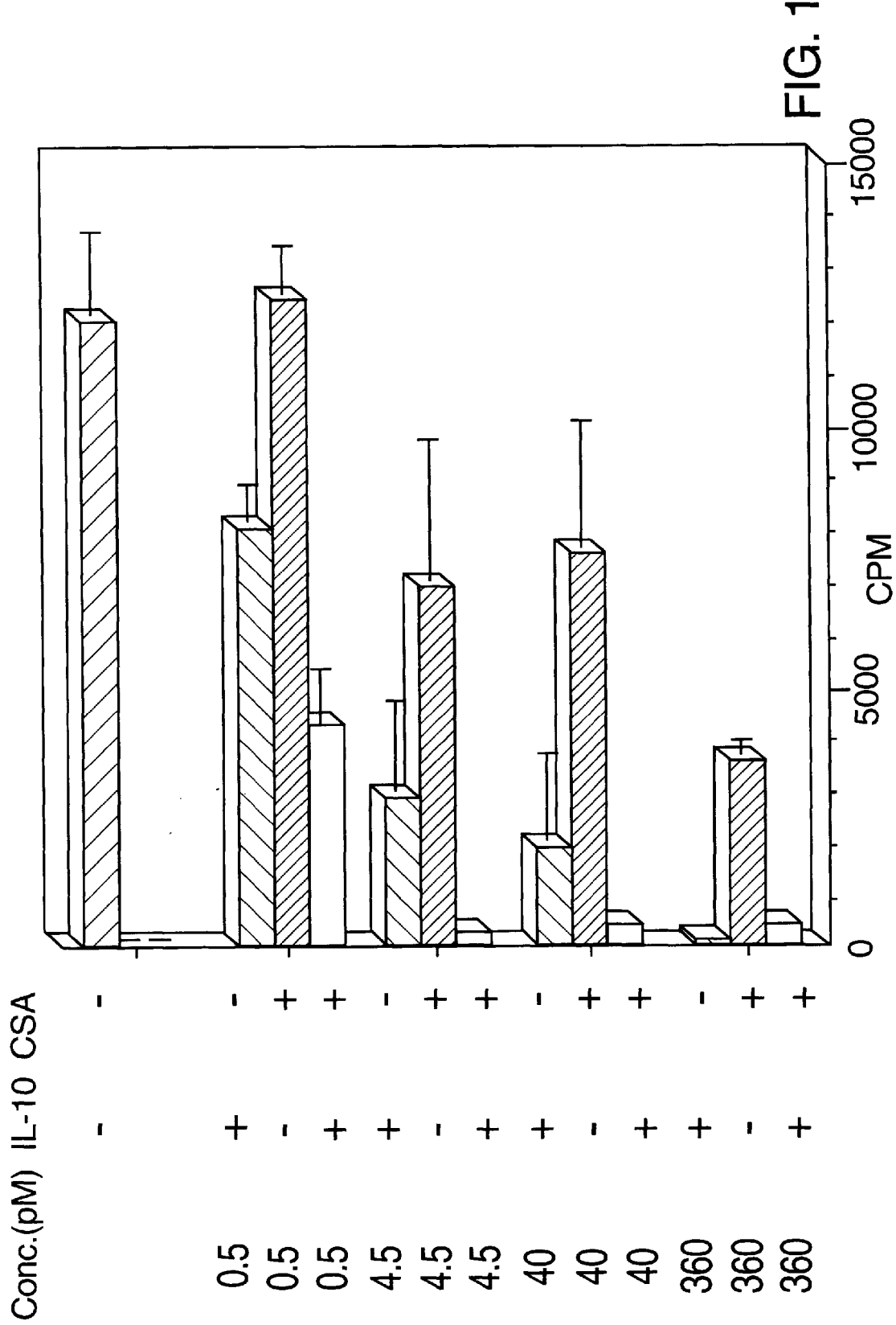

All references cited herein are hereby incorporated in their entirety by reference.

A failure of major organs is a principal cause of disease and death in mammals. Surgical replacement of a diseased organ, by transplantation with a normal organ obtained from another mammal of the same species, can be a life saving procedure. Unfortunately, normal bodily immune defense mechanisms recognize such organ transplants as foreign and attack them, resulting in graft failure and rejection. As such, a major impediment to transplantation of allogeneic tissues and organs is graft rejection by the transplant recipient. The cell-mediated immune response of the recipient, or host, to the donor tissue plays an important role in the rejection process. This response has two important phases: (i) recognition of the donor cells or tissue as "foreign" in the context of the major histocompatibility complex (MHC); and (ii) destruction of the foreign cells by the host cells. As part of this process, a number of host cells undergo proliferation and acquire cytotoxicity —that is, the ability to kill donor cells displaying the appropriate antigens. Thus, cell-mediated immunity can be described in terms of two measurable functions: proliferation, and cytotoxic activity—see Dubey et al., chapter 131 in Rose et al., Editors, "Manual of Clinical Laboratory Immunology", 3d edition (American Society of Microbiology, Washington, D.C., 1986).

Development of cell culture techniques has led to the establishment of in vitro methods that mimic the in vivo immunization process, thus providing measures for the assessment of cell-mediated immunity in vitro. Of particular utility in regard to transplantation is the mixed lymphocyte reaction (MLR), or mixed lymphocyte culture. Basically, MLR comprises co-culturing a sample of responder cells and a sample of inactivated stimulator cells such that the stimulator cells are allogeneic with respect to the responder cells (i.e., the stimulator cells are obtained from a different person from that from whom the responder cells are taken, and measuring the proliferative response of the responder cells. More specifically, MLR consists of mixing responder lymphocytes (mimics host cells) in a suitable culture system with stimulator lymphocytes (mimics donor cells), the proliferation and/or transcription machinery of which has been disabled, e.g. by irradiation or treatment with a DNA synthesis inhibitor (e.g., mitomycin C) or the like. The stimulator cells are inactivated so that they can still carry out their stimulatory function but are inhibited from any other functions that could obscure the response measured from the responder cells, i.e., the stimulator cells are treated so that they are incapable of replication, but their antigen processing machinery remains functional.

After the cells have been cultured for several days, a number of different measurements can be made to quantify the degree of reactivity of the responder cells to the stimulator cells. Usually, the response measured in the responder cells is cellular proliferation. Proliferation of the responder cells may be determined by the uptake of tritiated thymidine using standard protocols. For example, from $2.5-10 \times 10^4$ stimulator cells are added to $2.4 \times 10^4$ allogeneic CD4$^+$ (responder) cells in 96-well round-bottom tissue-culture plates and are incubated for 4 days in an appropriate medium. After incubation, the cells are pulsated with 1 $\mu$Ci of tritiated thymidine for 6 hours, and then they are harvested and measured for tritiated thymidine uptake, e.g., by scintillation counting.

It has unexpectedly been discovered that the combined/concurrent administration of IL-10 and CSA, or IL-10 and a CSA analogue, causes a synergistic suppression of T cell proliferation. Surprisingly, this synergistic effect is seen only when relatively low levels of these agents are used together. While the invention will hereinafter be discussed in terms of the combined use of IL-10 and CSA, it is to be understood that an analogue of CSA may also be combined with IL-10 to cause synergistic suppression of T cell proliferation, and that such combinations are contemplated for use in the practice of this invention.

The combination of IL-10 and CSA can advantageously be used in the suppression of pathology, associated with T cell responses, in particular, autoimmune diseases, graft-versus-host disease (GVHD) and tissue graft rejection. The invention can be used to suppress cell-mediated reactions such as allograft rejection and GVHD. Moreover, considering the diverse biological activities of IL-10, the concurrent use of IL-10 and CSA may support GVL (graft-versus-leukemia) in allogeneic bone marrow transplants.

The invention may be used to prevent the rejection or prolong the survival of allogeneic transplants of skin, heart, kidney, pancreas, bone marrow, small intestine, lung, etc.; to treat autoimmune diseases such as, for example, rheumatoid arthritis, lupus, diabetes mellitus, multiple sclerosis and myasthenia gravis; and to treat other diseases where CSA has been used, such as psoriasis. Due to the activity of IL-10, CSA can by used in lower amounts, thereby avoiding or reducing the serious side effects normally associated with the use of this drug.

Transplant recipients may be recipients of kidney, liver, heart, heart-lung, bone marrow, cornea transplant, etc. The transplanted tissue itself is typically human in origin but may also be from another species such as a rhesus monkey, baboon or pig. As used herein, the term "tissue" includes individual cells, such as blood cells, including progenitors and precursors thereof, and pancreatic cells, as well as solid organs and the like. The term solid organ means a heart, skin, a liver, a lung, a kidney, a pancreas, an intestine, endocrine glands, a bladder, skeletal muscles, etc.

The methods of the invention can be used prophylactically or for treatment of established autoimmune disease, GVHD or graft rejection. Individuals suitable for treatment by the methods of the invention include any individual at risk (predisposed) for developing GVHD or tissue rejection, i.e., a transplant patient, or an individual exhibiting clinical symptoms. Prophylactic use encompasses administration prior to transplantation as well as post-transplantation administration in the absence of any clinical symptoms of GVHD or graft rejection, to prevent or postpone onset of disease/rejection.

In the practice of the invention, IL-10 and CSA are to be "concurrently" administered to a patient. Concurrently administering means the IL-10 and CSA are administered to the subject either (a) simultaneously in time (optionally by formulating the two together in a common carrier), or (b) at different times during the course of a common treatment schedule. In the latter case, the two compounds are administered sufficiently close in time to achieve the intended effect. Typically, if one agent is administered within about the half-life of the first agent, the two agents are considered to be concurrently administered. The active agents may be administered together in a single pharmaceutical composition or separately. Both active agents (i.e., IL-10 and CSA) should be present in the patient at sufficient combined levels to be therapeutically effective. The routes of administration of the IL-10 and CSA may be the same or different.

Generally, IL-10 and CSA are administered as a pharmaceutical composition comprising an effective amount of IL-10 and CSA in a pharmaceutical carrier. A pharmaceutical carrier can be any compatible, non-toxic substance suitable for delivering the compositions of the invention to a patient.

As used herein, interleukin 10 or IL-10 is defined as a protein which (a) has an amino acid sequence substantially identical to a known sequence of mature (i.e., lacking a secretory leader sequence) IL-10 as disclosed in International Application Publication No. 91/003249, and (b) has biological activity that is common to native IL-10. For the purposes of this invention, both glycosylated (e.g., produced in eukaryotic cells such as yeast or CHO cells) and unglycosylated e.g., chemically synthesized or produced in *E. coli*) IL-10 are equivalent and can be used interchangeably Also included are muteins and other analogs, including viral IL-10, which retain the biological activity of IL-10.

IL-10 suitable for use in the invention can be obtained from a number of sources. For example, it can be isolated from culture media of activated T-cells capable of secreting the protein. Additionally, the IL-10 or active fragments thereof can be chemically synthesized using standard techniques known in the art. See, e.g., Merrifield, 1986, *Science* 233:341–347 and Atherton et al., *Solid Phase Peptide Synthesis, A Practical Approach,* 1989, IRL Press, Oxford.

Preferably, the protein or polypeptide is obtained by recombinant techniques using isolated nucleic acids encoding the IL-10 polypeptide. General methods of molecular biology are described, e.g., by Sambrook et al., 1989, *Molecular Cloning, A Laboratory Manual,* , 2d Ed., Cold Spring Harbor, N.Y. and Ausubel et al. (eds). *Current Protocols in Molecular Biology*, Green/Wiley, New York (1987 and periodic supplements). The appropriate sequences can be obtained using standard techniques from either genomic or cDNA libraries. DNA constructs encoding IL-10 may also be prepared synthetically by established standard methods, e.g., in an automatic DNA synthesizer, and then purified, annealed, ligated and cloned in suitable vectors. Atherton et al., 1989. Polymerase chain reaction (PCR) techniques can be used. See e.g., *PCR Protocols: A Guide to Methods and Applications,* 1990, Innis et al. (ed.), Academic Press, New York.

The DNA constructs may contain the entire native sequence of IL-10 or a homologue thereof. The term "homologue" is intended to indicate a natural variant of the DNA sequence encoding IL-10 or a variant or fragment produced by modification of the DNA sequence. Examples of suitable modifications of the DNA sequence are nucleotide substitutions which do not give rise to another amino acid sequence or nucleotide substitutions which do give rise to a different amino acid sequence and therefore, possibly, a different protein structure. Other examples of possible modifications are insertions of one or several nucleotides into the sequence, addition of one or several nucleotides at either end of the sequence, or deletion of one or several nucleotides at either end or within the sequence. Any homologous DNA sequence encoding a protein which exhibits IL-10 activity (e.g., with respect suppression of T cell proliferation) similar to that of the naive protein is contemplated for use in the claimed invention.

The nucleotide sequences used to transfect the host cells can be modified, as described above, to yield IL-10 muteins and fragments with a variety of desired properties. Such modified IL-10 can vary from the naturally-occurring sequence at the primary level, e.g., by amino acid insertions, substitutions, deletions and fusions. Preferably, amino acid substitutions will be conservative; i.e., basic amino acid residues will be replaced with other basic amino acid residues, etc. These modifications can be used in a number of combinations to produce the final modified protein chain.

Amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants, e.g., glycosylation variants or proteins which are conjugated to polyethylene glycol (PEG), etc. Such variants can be used in this invention as long as they retain the biological activity of IL-10.

Preferably, human IL-10 is used for the treatment of humans, although viral or mouse IL-10, or IL-10 from some other mammalian species, could be used instead. Most preferably, the IL-10 used is recombinant human IL-10. Recombinant production of human IL-10 is described in U.S. Pat. No. 5,231,012. Preparation of human and mouse IL-10 has been described in International Application Publication No. WO 91/00349. The cloning and expression of viral IL-10 (BCRFI protein) from Epstein Barr virus has been disclosed by Moore et al. (*Science* 248:1230,1990), and is described in EP 0 506 836.

CSA may be is administered in a manner as is conventionally practiced. See, e.g., Goodman and Gilman's The Pharmacological Basis of Therapeutics, 7th Ed, 1985, p. 1299. For example, CSA may be provided as an oral solution of 100 mg/ml with 12.5% alcohol, and for intravenous administration as a solution of 50 mg/ml with 33% alcohol and 650 mg of polyoxyethlated castor oil. When administered intravenously, CSA may be given as a dilute solution of 50 mg to 20–100 mg of normal saline or 5% dextrose in water, by slow infusion over a period of several hours. The intravenous dose is typically one third of the oral dose. Most preferably, administration of CSA is orally, either in capsule or tablet form. Such formulations may be prepared by any suitable method of pharmacy which includes the step of bringing into association the active compound and a suitable carrier (which may contain one or more accessory ingredients). In general, the formulations can be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules containing the active compound, optionally mixed with a binder, lubricant, inert diluent, and/or surface active dispersing agent(s). Molded tablets may be made by molding, in a suitable machine, the powdered compound moistened with an inert liquid binder. The preparation of CSA is disclosed in U.S. Pat. No. 4,117,118. CSA which may be used in the practice of the invention is commercially available under the name SANDIMMUNE® from Sandoz Pharmaceuticals Corporation.

Synergistic suppression of T cell proliferation may also be observed using IL-10 and an analogue of CSA. As used herein, a "CSA analogue" is meant to include synthetic analogues as well as any agent which exhibits the same activity/mechanism of action as CSA. Such agents include, for example, FK-506. FK-506 is a macrolide immunosuppressant isolated from *Streptomyces tsukubaenis*, no. 9993. EP 0 184 162 (Fujisawa).

Administration of IL-10 is preferably parenteral by intraperitoneal intravenous, subcutaneous or intramuscular injection of infusion or by an other acceptable systemic method. Administration by intramuscular or subcutaneous injection is most preferred. Alternatively, the IL-10 may be administered by an inplantable or injectable drug delivery system. See, e.g., Urquhart et al, 1984, *Ann Rev. Pharacol. Toxicol* 24:199; Lewis, ed., 1981, *Controlled Release of Pesticides and Pharmaceuticals*, Plenum Press, New York, N.Y.: U.S. Pat. Nos. 3,773,919, and 3,270,960. Oral administration may also be carried out, using well known formulations which protect the IL-10 from gastrointestinal proteases.

Compositions useful for parenteral administration of such drugs are well known. See, e.g., Remington's Pharmaceutical Science, 11th Ed., 1990, Mack Publishing Co., Easton, Pa. When administered parenterally, the IL-10 is typically formulated in a unit dosage injectable form (solution, suspension, emulsion) in association with a pharmaceutical carrier. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other source proteins at a concentration in the range of about 5 to 20 μg/ml. Any of the well known carrier proteins such as human serum albumin can also be added if desired.

IL-10 can also be delivered by standard gene therapy techniques, including e.g., direct DNA injection into tissues, the use of recombinant viral vectors or phospholipid and implantation of transfected cells. See, e.g., Rosenberg, 1992, J. Clin. Oncol. 10:180.

IL-10 and CSA are concurrently administered to a human patient in an amount effective to provide an immunosuppressive effect. As used herein "effective amount" means an amount sufficient to reduce or prevent GVHD, an autoimmune disease or tissue rejection, and refers to the combined effects of the two agents working in concert. One or both agents may, for example, be used at a dose which, if used alone, would be considered suboptimal for the intended purpose. The effective amount for a particular patient may vary depending on such factors as the state, type, and amount of tissue transplanted, the overall health and age of the patient, the route of administration, the severity of observed side-effects, and the like. The effective dose of IL-10 typically will range from about 0.1–25 μg/kg/day, preferably about 1–16 μg/kg/day. The effective dose of CSA typically will range of from about 1–14 mg/kg/day, more preferably from about 1–8 mg/kg/day. Preferably, administration is to begin simultaneously with transplantation, or 2 to 4 hours before transplantation. Administration may, however, begin within the 24-hour period preceding transplantation or within the 24-hour period following transplantation. It is also contemplated that administration can be started at any time after transplantation to replace or supplement other compounds being administered to a patient to prevent graft rejection. The length of administration may vary and, in some cases, may continue over the remaining lifetime of a patient, to control graft rejection processes.

EXAMPLES

This invention can be illustrated by the following non-limiting examples:

General Materials and Methods

In the experiments described below, the following protocols and procedures were followed:

Media

Cells were prepared and cultured in RPMI 1640 (JRH Biosciences, Lenexa, Kans.), supplemented with 10% fetal calf serum (Hazleton Biologics, Inc., Lenexa, Kans.), 2 mM L-glutamine (JRH Biosciences, Lenexa, Kans.), 80 μgml gentamicin (Sigma Chemical Co., St. Louis, Mo.) or 100 u/mi penicillin-streptomycin (JRH Biosciences, Lenexa, Kans.).

ELISA

ELISA kits for cytokine production determination were purchased from R&D systems, Minneapolis, Minn.

Human PBMC and Monocyte Purification

Human blood samples were collected in heparinized vacutainers. To facilitate removal of red blood cells (RBC), 2 ml of 6% dextran in phosphate buffered saline (PBS) (JRH Biosciences, Lenexa, Kans.) was added to each vacutainer, mixed and allowed to stand at room temperature for 30–45 min. The top buffy coat layer was carefully removed and cells centrifuged (300×g, 10 min., 4° C.). The cells were washed 3 times in 15 ml PBS. The peripheral blood mononuclear cells (PBMC) were isolated using a FICOLL-PAQUE (Pharmacia, Piscataway, N.J.) gradient. Ten ml of cells were layered on top of 4 ml FICOLL-PAQUE, centrifuged (1400×g, 20 min., room temperature) and the cells sedimenting at the interface were collected. These PBMC were washed 3 times in PBS, enumerated and resuspended in appropriate media for use in MLR experiments. In some of the experiments peripheral blood monocytes were prepared by incubating PBMC in medium supplemented with 10% fetal bovine serum (FBS) and allowing adherence for 1 hour and 37° C. in 5% $CO_2$ atmosphere in T-75 flasks each containing $10^7$ PBMC. After removing the nonadherent cells, the flasks were extensively washed with warm medium, then incubated with cold PBS on ice for 15 minutes. Adherent monocytes were subsequently recovered by repeated pipetting, washed and resuspended in complete medium. Cell purity determined by staining with CD14 monoclonal antibodies and flow microfluorometric (FMF) analysis was 92% $CD14^+$. Viability determined by trypan blue exclusion was >95%.

Mixed Lymphocyte Reaction

The stimulator PBMAC were treated with 50 μl mitomycin C (Sigma Chemical Co., St. Louis, Mo.) for 20 minutes at 37° C. The responder PBMC and the stimulator cells were added to a 96-well microtiter plate (Becton Dickinson, Lincoln Park, N.J.) at $1×10^5$ cells per well of each, along with cytokines or antibodies in a total volume of 200 μl in triplets. The cultures were incubated at 37° C. with 5% $CO_2$ in air for 6 days. The cultures were then pulsed with 1 μCi [$^3$H]TdR (15.6CI/mmol, NEN, Boston, Mass.) per well for 16 hours. The cells were harvested onto a filter using a 96-well cell harvestor (Skatron, Inc., Sterling, Va.) and counted on a beta counter (Pharmacia LKB Nuclear Inc., Gaithersburg, Md.).

Immunofluorescence and Flow Cytometry

The supernatant from the MLR was removed and the non-adherent PBMC harvested. The adherent cells were harvested by incubation with 5 mM EDTA at 4° C. for 20 minutes and gently scraped. Cells were combined, centrifuged at 300×g for 10 minutes and washed 3 times in ice-cold PBS. The viable cells were enumerated by Trypan Blue exclusion using a Neubaeur counting chamber, resuspended to $1×10^7$ cell/ml in PBS and 100 μl of human IgG (1 mg/ml) was added to each well and incubated on ice. Thirty minutes later, 100 μl/well FBS was added and the plate centrifuged at 500×g for 10 minutes. The supernatant was removed and the cells were resuspended in the appropriate amounts of mouse-anti-human monoclonal antibodies coupled to FITC. For dual-stained samples, cells were concurrently incubated with 20 μl of mouse-anti-human monoclonal antibodies to each surface marker. All volumes were made up to 40 μl with PBS. Isotypic control antibodies were used at the same concentration as the specific markers. Samples were incubated for 30 minutes at 4° C., FBS was added (100 μl/well), and the samples were centrifuged as previously described. Cells were washed 3 times in 200 μl aliquots of PBS, containing 50% FBS, and resuspended in 1 ml of PBS containing 0.01% sodium azide. Flow cytometric analysis was performed using a FACScan flow cytometer (Becton Dickinson Immunocytometry Systems (BDIS), San Jose, Calif.) and viable cells gated, based upon propidium iodide exclusion. Mean channel fluorescence and percent positives for specific markers were determined using LYSIS II software (BDIS). For purifying B cells and monocytes, PBMC were respectively stained with CD20 or CD14 and sorted by positive selection. Purity of the sorted cells ranged between 95 and 98% in three experiments.

Depletion of Antigen Presenting Cells from Human PBMC

Purified PBMC from human blood were collected in heparinated tubes by FICOLL gradient. The blood was diluted 1:1 with PBS. 30 ml of the diluted blood was laid on top of 20 ml Ficoll in a 50 ml conical tube and spun at 2,000 rpm for 30 minutes. The interface cells were collected and washed 3 times with medium (10% FCS/RPMI).

The plastic adherent antigen presenting cells (APC) were removed by resuspended PBMC in 1%. human serum (Type AB) at $1 \times 10^6$ cells/ml, and incubated at 37° C. for 30 min. The cells which floated were collected and placed in media (10% FCS/RPMI).

Nylon wool adherent APC were removed as follows:

A 10 ml syringe was packed with 1.5 g of nylon wool (Polysciences, Inc., Cat. #18369) and autoclaved. A 3-way stopcock and a 22-gauge needle were attached to the syringe, and the column was washed with 50 ml of pre-warmed medium. A cell suspension of $5 \times 10^7$ cells/ml of plastic adherent APC was prepared in prewarmed medium. Just before adding the cell suspension, the wool was rinsed with 5 ml of prewarmed medium, the column was left to run dry, and the stopcock was closed. Cells ($5-10 \times 10^7$) were added. The cells were allowed to penetrate the column, and the stopcock was closed. An additional 0.5 ml of medium was added and the column maintained at 37° C. for 45 minutes. Nonadherent cells were collected into a tube by washing the column with 20 ml of prewarmed medium, eluted at 1 drop per second.

Demonstration of Immunosuppressive Effects

A major property of IL-10 is the ability to inhibit cell-mediated immunity by blocking production of cytokines of the Th 1 type (IL-2, IFN) and monocytes (TNF-α). Since these cytokines are known to be the major regulators of graft acceptance and graft versus host disease (GVHD), the effect of human IL-10 (hIL-10) on the allogeneic stimulation of T cells was investigated.

IL-10 Suppresses MLR-induced Proliferation

To assess the effect of IL-10 on T-cell proliferation induced by alloantigen, the effect of IL-10 on the proliferative response evoked in the primary one-way MLR, where peripheral blood mononuclear cells (PBMC) from one donor were co-cultured with mitomycin-treated PBMC of an unrelated donor with and without IL-10 was examined.

In 20 independent experiments using PBMC from 16 unrelated donors, IL-10 (100–200 U/ml) strongly suppressed MLR-induced proliferation. In these studies, the allogeneic stimulation induced a strong proliferative response and the suppression by IL-10 ranged between 65% and 100% regardless of the stimulation index of the MLR. Table 1 shows that a monoclonal antibody to IL-10 neutralized IL-10 -induced suppression of MLR. The suppression observed in these cultures was attributable to IL-10, since the addition of neutralizing monoclonal antibody, but not its isotypic control, reversed the IL-10 suppressive effect .

TABLE 1

| Culture[a] | CPM (mean ± SD)[b] |
|---|---|
| MLR | 5127 ± 935 |
| MLR + IL-10 | 643 ± 197 |

TABLE 1-continued

| Culture[a] | CPM (mean ± SD)[b] |
|---|---|
| MLR + IL-10 + 19B1 | 5035 ± 131 |
| MLR + IL-10 + rat.IgG1 | 486 ± 14427 |

[a]MLR cultures were set up as described above. Human IL-10 (100 U/ml), 19B1 (a rat monoclonal antibody to IL-10) and its isotypic control rat IgG1 were used at 2.5 U g/ml.
[b]Data are $^3$HTdR uptake M ± SD of triplicate determination and are representative of 3 experiments.

Inability of IL-10 to Inhibit Proliferation in MLR Induced by B Cell Lines is Associated With Lack of Inhibition of TNF-α Production Earlier investigation of the mechanism of action of IL-10 revealed that it suppresses activation of human T-cell clones induced by specific soluble antigens presented on normal monocytes but not when the antigens were presented by EBV-LCL B-cell lines. de Waal et al., 1991, *J Exp. Med.* 174:915–924. In these studies it was not clear whether the inability of IL-10 to suppress T-cell activation when EBV-LCLs were used was due to the fact they were B cells or to the possibility that these cells represented a different subpopulation, and/or that they were EBV-transformed B cells. To address this question further, the ability of IL-10 to suppress the proliferation in MLR when allogeneic PBMC, purified B cells, monocytes or B cell lines were used as stimulators was studied. Table 2 shows that IL-10 suppresses proliferation in MLR when normal B cells, but not B-cell lines, are used as stimulators.

TABLE 2

| | Addition to MLR[a]; CPM (M ± SD)[b] | | |
|---|---|---|---|
| MLR | Medium | IL-10 | CSA |
| PBMC + B | 3939 ± 100 | 182 ± 47 | ND |
| PBMC + JY | 26222 ± 6293 | 25182 ± 7302 | 7144 ± 263 |
| PBMC + Daudi | 37357 ± 4497 | 45763 ± 3089 | 14167 ± 2762 |

[a]MLR cultures were set up between PBMC ($1 \times 10^5$/well) and mitomycine treated B cell line ($1 \times 10^5$/well) or $4 \times 10^4$) purified B cells, positively selected CD20+ by FMF, as described above. Human IL-10 was used at 200 U/ml and cyclosporin A 40 ng/ml.
[b]Data are (3)HTdR uptake M ± SD of triplicate determination and are representative of 3 experiments.
ND = not done As shown in Table 2, IL-10 strongly suppresses the MLR-induced proliferation when purified normal B cells (985% CD20+) or monocytes (98% CD14+) were used as stimulators and PBMC as responder cells. However, IL-10 did not suppress the reaction when B cell lines (Daudi or JY), were uses as stimulators of the MLR. Higher doses of IL-10 up to 1000 U/ml did not suppress JY-induced MLR. These data suggest that the inability of IL-10 to suppress MLR induced by B-cell lines is not attributable to the fact that they are B cells but rather suggest the possibility that these cell lines may stimulate MLR via different mechanism (s) from that used by normal B cells.

As can be seen in Table 2, CSA inhibited proliferation in the JY-induced MLR.

To investigate the mechanism by which B cell line-induced MLR resists suppression by IL-10, the effect of IL-10 on cytokine synthesis in this MLR was examined. The presence of IL-2, IFN-γ and TNF-α in supernatants of MLR set up with and without IL-10 (200 U/ml) for 60 hours was determined using ELISA kits. Table 3 shows representative data from two experiments.

TABLE 3

| MLR[a] (R + S) | Cytokine concentration (pg/ml)[b] | | |
|---|---|---|---|
| | IFN-γ | IL-2 | TNF-α |
| PBMC JY | 5715 | 3006 | 154 |
| PBMC + JY + IL-10 | 2960 | 1294 | 209 |
| PBMC + JY + CSA | 509 | 720 | 84 |
| PBMC + PBMC | 200 | 120 | <25 |
| PBMC + PBMC + IL-10 | <25 | <50 | <25 |

[a]The MLR cultures were set up as described above using PBMC ($1 \times 10^6$/ml) as responder and mitomycin C-treated JY cells ($5 \times 10^5$ cell/) or allogeneic PBMC ($5 \times 10^5$) as stimulators in a 24-well plate for 60 hours. IL-10 was used at 100 U/ml and CSA at 40 ng/ml.
[b]Data are the means of triplicate determination (SD $\leq$ 15%) of cytokine concentrations detected in the supernatants of these cultures. Results are representative of 2 or 3 experiments. Detection limits of the commercial ELISA kits were 25 pg/ml for IFN-γ and TNF-α, and 50 pg/ml for IL-2.

Table 3 shows that high levels of cytokines were detectable in the supernatants of MLR induced by JY. In particular, this data shows that levels of IL-2 and IFN-γ but not that of TNF-α, are depressed in the supernatants of MLR set up with IL-10. In contrast, CSA inhibited TNF-α production.

Since supernatants of cultures of JY cells alone (treated or untreated with mitomycin C) did not contain detectable TNF-α, the source of TNF-α in these MLRs could be attributed to the activated responder PBMC. Together, the data suggest that the inability of IL-10 to inhibit proliferation in MLR between PM BC and JY may be due to the inability of IL-10 to inhibit TNF-α synthesis, which allow this cytokine to synergize with the residual IL-2 in these cultures and to overcome the IL-10-induced suppression. This conclusion is supported by the finding that CSA which, unlike IL-10, inhibits proliferation in the JY-induced MLR (Table 2), also inhibited TNF-α production in MLR (Table 3). The ability of CSA, but not IL-10 to suppress proliferation in the B-cell line-induced MLR, indicates a distinct mechanism of action by IL-10 verses CSA on allogeneic immune responses.

Comparison of the Potency of IL-10 and CSA

Since CSA also has a cytokine-synthesis inhibition ability and currently being used in most immunosuppressive protocols in organ transplantation, the activity of CSA was compared to that of IL-10.

Using an in vitro experimental model for allostimulation, the one-way mixed lymphocyte reaction (MLR), hIL-10 was found to be a more potent inhibitor than CSA (IC50: 8pM and 4nM respectively). Moreover, it was found that the addition of combinations of hIL-10 and CSA at low doses caused synergistic suppression of T cell proliferation in MLR.

As can be seen in the Figure, the addition of combinations of hIL-10 and CSA at certain doses (IL-10 and CSA: 0.5–40 picomolar of each) to MLR cultures caused synergistic suppression of T cell proliferation in MLR. At higher concentrations of each agent (360 pM) the synergy was lost. Synergistic suppression between IL-10 and CSA has been observed in in vivo studies.

IL-10 and CSA synergistically inhibited T cell activation in MLR. This synergy was observed at lower doses of hIL-10 and CSA. From this data it can be observed that the administration of a combination of IL-10 and CSA is a more effective suppressive therapy than either IL-10 or CSA individually.

Effect of IL-10 and CSA on Direct and Indirect Allostimulation

Allostimulation of T cell can be exerted via two pathways; direct allostimulation and indirect allostimulation. As used herein, "direct allostimulation" means the response of the recipient T cell to alloantigens as intact MHC molecules on the surface of allogeneic stimulator cells in the graft. Direct allostimulation is the cause of acute graft rejection and is the principal contributor to antigraft cytotoxic T cell response mediating early rejection episodes. "Indirect allostimulation," as used herein means the response of the recipient T cell graft major histocompatibility (MHC) alloantigens that have been processed and presented by the recipients' APC. Indirect allostimulation the cause of chronic allograft rejection and antigraft antibody production, xenograft rejection, and induction of unresponsiveness (tolerance).

The effect of hIL-10 and CSA on these two pathways of allostimulation was studied. Direct allostimulation which results from the interaction of the T cell with allo MHC molecules on the stimulator cells is thought to be responsible for the early acute graft rejection. Indirect allostimulation which results from T cell interaction with shed alloantigen of the stimulator cells presented by the recipient (APC) is thought to be responsible for the late graft rejection. To examine the effect of IL-10 and CSA on the direct allostimulation, a one way primary MLR was set up in which PBMCs of the responder were depleted of APC's and cultured with PBMCs of the stimulator. Addition of IL-10 to these cultures caused more suppression than CSA. Similar results were obtained when CD4+ or CD8+ cells were used as responders in these cultures.

For the indirect allostimulation, the APC's were depleted from the stimulator population and cultured with PBMCs of the responder hIL-10 was also stronger inhibitor to the indirect allostimulation than CSA.

Human IL-10 was found to be more effective than CSA in suppressing both the direct allostimulation and the indirect allostimulation of T cells. Since hIL-10 suppresses both the direct and the indirect T cell allostimulation, a combination of IL-10 and (CSA can be used to prevent acute graft rejection (mediated by the direct allostimulation), and chronic graft and xenograft rejedction (mediated by the indirect allostimulation).

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A method of suppressing or preventing graft-versus-host disease comprising administering a synergistically effective amount of low doses of interleukin 10 and cyclosporin to a individual at risk for or afflicted with graft-versus-host disease.

2. The method of claim 1 wherein the interleukin 10 is human interleukin 10.

3. The method of claim 1 wherein the interleukin 10 is viral interleukin 10.

4. The method of claim 1 wherein the interleukin 10 and cyclosporin are administered to the individual receiving a transplant.

5. A method of suppressing or preventing graft rejection comprising administering a synergistically effective amount of low doses of interleukin 10 and cyclosporin to an individual at risk of or experiencing tissue transplant rejection.

6. The method of claim 4 wherein the interleukin 10 and cyclosporin are administered to the individual prior to receiving a tissue transplant.

7. The method of claim 4 wherein the interleukin 10 is human interleukin 10.

8. The method of claim 4 wherein the interleukin 10 is viral interleukin 10.

9. A method of treating autoimmune disease comprising administering a synergistically effective amount of low doses of interleukin 10 and cyclosporin to a individual afflicted with an autoimmune disease.

10. The method of claim 9 wherein the interleukin 10 is human interleukin 10.

11. The method of claim 9 wherein the interleukin 10 is viral interleukin 10.

12. A pharmaceutical composition comprising, a synergistic combination of low doses of interleukin 10 and cyclosporin and a pharmaceutical acceptable carrier.

13. The composition of claim 12 wherein the interleukin 10 is human interleukin 10.

14. The composition of claim 12 wherein the interleukin 10 is viral interleukin 10.

* * * * *